US008594769B2

(12) United States Patent
Mostafavi (10) Patent No.: US 8,594,769 B2
(45) Date of Patent: Nov. 26, 2013

(54) SYSTEMS AND METHODS FOR ASSOCIATING PHYSIOLOGICAL DATA WITH IMAGE DATA

(75) Inventor: Hassan Mostafavi, Los Altos, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 1727 days.

(21) Appl. No.: 11/863,602

(22) Filed: Sep. 28, 2007

(65) Prior Publication Data

US 2009/0088622 A1    Apr. 2, 2009

(51) Int. Cl.
*A61B 5/00* (2006.01)
(52) U.S. Cl.
USPC ........... 600/428; 600/407; 600/410; 600/413; 600/425; 600/436; 382/128
(58) Field of Classification Search
USPC ................. 600/407, 413, 428, 425; 382/128
See application file for complete search history.

(56) References Cited

U.S. PATENT DOCUMENTS

| | | | | |
|---|---|---|---|---|
| 6,073,041 | A * | 6/2000 | Hu et al. | 600/410 |
| 7,177,386 | B2 | 2/2007 | Mostafavi et al. | |
| 7,454,043 | B2 * | 11/2008 | Eck et al. | 382/128 |
| 7,513,875 | B2 * | 4/2009 | Kushnir et al. | 600/538 |
| 2004/0081269 | A1 * | 4/2004 | Pan et al. | 378/4 |
| 2005/0234331 | A1 * | 10/2005 | Sendai | 600/425 |
| 2006/0241443 | A1 | 10/2006 | Whitmore et al. | |
| 2007/0081704 | A1 * | 4/2007 | Pan et al. | 382/128 |
| 2007/0127789 | A1 * | 6/2007 | Hoppel et al. | 382/128 |

FOREIGN PATENT DOCUMENTS

WO    2009 042936 A1    4/2009

OTHER PUBLICATIONS

International Search Report and Written Opinion for international Application No. PCT/US2008/077978, Dated Dec. 3, 2008.

* cited by examiner

*Primary Examiner* — Unsu Jung
*Assistant Examiner* — Amanda Lauritzen Moher
(74) *Attorney, Agent, or Firm* — Vista IP Law Group, LLP (57) ABSTRACT

A method of processing image data that includes obtaining image data, determining a phase of a respiratory cycle, and associating the image data with the determined phase within 60 seconds, and more preferably, within 15 seconds, after the image data is obtained. A system for processing image data that includes a processor configured for obtaining image data, determining a phase of a respiratory cycle, and associating the image data with the determined phase within 60 seconds, and more preferably, within 15 seconds, after the image data is obtained. A method of processing image data that includes obtaining image data during an image acquisition session, determining a phase of a respiratory cycle, and associating the image data after the image data is obtained but before the image acquisition session is completed.

50 Claims, 6 Drawing Sheets

SYSTEMS AND METHODS FOR ASSOCIATING PHYSIOLOGICAL DATA WITH IMAGE DATA

FIELD

This application relates to systems and methods for associating physiological data with image data.

BACKGROUND

A variety of imaging techniques are currently being used in the medical field. For examples, positron emission tomography, single photon emission computed tomography, and computed tomography, are some of the examples of the imaging techniques that are commonly used.

Positron emission tomography (PET) detects photons generated through positron-electron annihilation of positrons from a radioactive tracer placed in the object, e.g., patient, to be imaged, and analyzes the photon energy and trajectory to generate tomographic images of the patient. Single photon emission computed tomography (SPECT) generates images by computer analysis of photon emission events from a radioactive tracer. Positron-electron annihilation may be the source of such photon emission. PET and SPECT require the detection and analysis of single photon events. Photomultipliers are generally used for single photon event detection in PET and SPECT.

Computed tomography is an imaging technique that has been widely used in the medical field. In a procedure for computed tomography, an x-ray source and a detector apparatus are positioned on opposite sides of a portion of a patient under examination. The x-ray source generates and directs a x-ray beam towards the patient, while the detector apparatus measures the x-ray absorption at a plurality of transmission paths defined by the x-ray beam during the process. The detector apparatus produces a voltage proportional to the intensity of incident x-rays, and the voltage is read and digitized for subsequent processing in a computer. By taking thousands of readings from multiple angles around the patient, relatively massive amounts of data are thus accumulated. The accumulated data are then analyzed and processed for reconstruction of a matrix (visual or otherwise), which constitutes a depiction of a density function of the bodily section being examined. By considering one or more of such sections, a skilled diagnostician can often diagnose various bodily ailments such as tumors, blood clots, etc.

Some radiation therapy linacs are equipped with a diagnostic quality x-ray imaging system. The flat panel x-ray detector and KV x-ray source are attached to the linac gantry and rotate with the gantry around the patient. This imaging system is used to locate and target tumors and sensitive organs around the tumor inside the body. This increases the accuracy of targeting the linac treatment beam at the target, while avoiding the surrounding healthy tissue. One method of 3D imaging using such systems is cone beam CT imaging where of 2D x-ray projections acquired as the gantry rotates around the patient. Using cone beam CT reconstruction, a 3D image of patient anatomy is formed.

PET, SPECT, and Computed tomography has found its principal application to examination of bodily structures or the like which are in a relatively stationary condition. However, currently available PET, SPECT, and computed tomographic apparatus may not be able to generate images with sufficient quality or accuracy due to physiological movement of a patient. For example, beating of a human heart and breathing have been known to cause degradation of quality in PET, SPECT, and CT images.

Degradation of quality of images due to patient's breathing is more difficult to address than that associated with heart motion. Patients' breathing poses a unique problem to imaging that is different from heart motion. This is because the pattern and the period of a patient's breathing cycle is generally less consistent when compared to those of the patient's cardiac cycle. As such, while a particular phase of a cardiac cycle may be predicted with sufficient accuracy, a particular phase of a breathing cycle may not be as easily predicted or determined.

Currently, to account for a patient's breathing during an image acquisition session, the patient's breathing motion is measured and recorded while image data are obtained. After all of the image data are collected, the breathing motion data are analyzed to determine phases of a respiratory cycle. The determined phases are then associated with the image data (e.g., PET, SPECT, or CT image data) such that image data generated at the same phase of the respiratory cycle are associated with the same phase. In existing systems, all of the image data are obtained before they are subsequently associated with the motion data. However, the wait time for finishing the image acquisition process can be quite long, especially for the case of PET imaging. In PET imaging, the list mode of image data acquisition may take up to 45 minutes. As a result, image data that are associated with motion data (e.g., binned image data) may not be available to a physician until a long time (e.g., sometimes in the order of minutes) after the image data is acquired.

In the case of respiratory correlated, or 4D, cone beam CT, the acquired 2D projections are associated with a discrete and finite set of periodic breathing phase intervals called phase bins. A separate 3D image is formed by reconstructing from the projections corresponding to each phase bin. The sequence of 3D images corresponding to the designated phase bins are called 4D cone beam CT images. In order to have a more uniform distribution of projections corresponding to a bin on the gantry rotation circle, the gantry rotation speed is reduced such that acquisition of projections can take several minutes. Again, waiting for the completion of acquisition of the projection images before reconstruction of images begins can take a very long time.

For the foregoing, improved system and method for processing image data, and more particularly, for associating physiological data with image data, would be desirable.

SUMMARY

In accordance with some embodiments, a method of processing image data that includes obtaining image data, determining a phase of a respiratory cycle, and associating the image data with the determined phase within 60 seconds, and more preferably, within 15 seconds, after the image data is obtained.

In accordance with other embodiments, a system for processing image data that includes a processor configured for obtaining image data, determining a phase of a respiratory cycle, and associating the image data with the determined phase within 60 seconds after the image data is obtained.

In accordance with other embodiments, a method of processing image data that includes obtaining image data during an image acquisition session, determining a phase of a respiratory cycle, and associating the image data after the image data is obtained but before the image acquisition session is completed.

In accordance with other embodiments, a system for processing image data that includes a processor configured for obtaining image data during an image acquisition session, determining a phase of a respiratory cycle, and associating the image data after the image data is obtained but before the image acquisition session is completed.

Other aspects and features will be evident from reading the following detailed description of the preferred embodiments, which are intended to illustrate, not limit, the invention.

BRIEF DESCRIPTION OF THE DRAWINGS

The drawings illustrate the design and utility of preferred embodiments, in which similar elements are referred to by common reference numerals. In order to better appreciate how advantages and objects of the embodiments are obtained, a more particular description of the embodiments will be illustrated in the accompanying drawings.

DETAILED DESCRIPTION OF THE EMBODIMENTS

Various embodiments are described hereinafter with reference to the figures. It should be noted that the figures are not drawn to scale and elements of similar structures or functions are represented by like reference numerals throughout the figures. It should also be noted that the figures are only intended to facilitate the description of specific embodiments. They are not intended as an exhaustive description of the invention or as a limitation on the scope of the invention. In addition, an aspect described in conjunction with a particular embodiment is not necessarily limited to that embodiment and can be practiced in any other embodiments.

Figure 1:
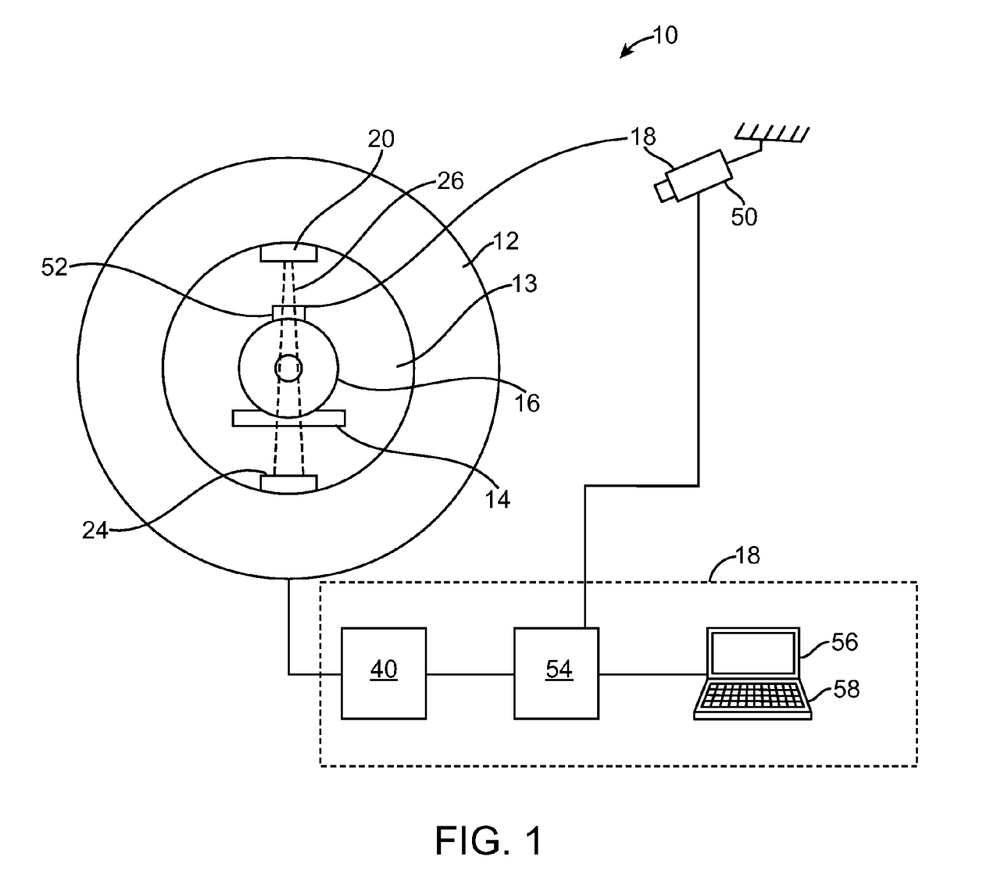
FIG. 1. illustrates a computed tomography system in accordance with some embodiments.

Referring now to the drawings, in which similar or corresponding parts are identified with the same reference numeral, FIG. 1 illustrates a computed tomography (CT) image acquisition system 10 in accordance with some embodiments. The system 10 includes a gantry 12, a panel 14 for supporting a patient 16, and a position monitoring system 18. In the illustrated embodiment, the gantry 12 has a ring configuration and includes a bore 13. In other embodiments, the gantry 12 can have other configurations, e.g., a C-arm configuration. The gantry 12 includes a radiation source 20 that projects a beam 26 (e.g., a fan beam, a cone beam, etc.) of radiation towards a detector 24 on an opposite side of the gantry 12 while the patient 16 is positioned at least partially between the radiation source 20 and the detector 24. The detector 24 has a plurality of sensor elements configured for sensing radiation that passes through the patient 16. Each sensor element generates an electrical signal representative of an intensity of the radiation as it passes through the patient 16.

During a scan to acquire image data (i.e., CT image data), the gantry 12 rotates about the patient 16 while the position monitoring system 18 monitors a position of at least a portion of the patient 16. In the illustrated embodiment, the position monitoring system 18 includes an optical device 50, a marker block 52, and a processor 54. The position monitoring system 18 may also include a monitor 56 for displaying data and an input device 58, such as a keyboard or a mouse, for inputting data. The processor 54 is coupled to the optical device 50 and a gantry rotation control 40. The rotation of the gantry 12 and the operation of the radiation source 20 are controlled by the gantry rotation control 40, which provides power and timing signals to the radiation source 20 and controls a rotational speed and position of the gantry 12 based on signals received from the optical device 50 or the processor 54. Although the control 40 is shown as a separate component from the gantry 12 and the processor 54, in alternative embodiments, the control 40 can be a part of the gantry 12 or the processor 54.

Figure 2A:
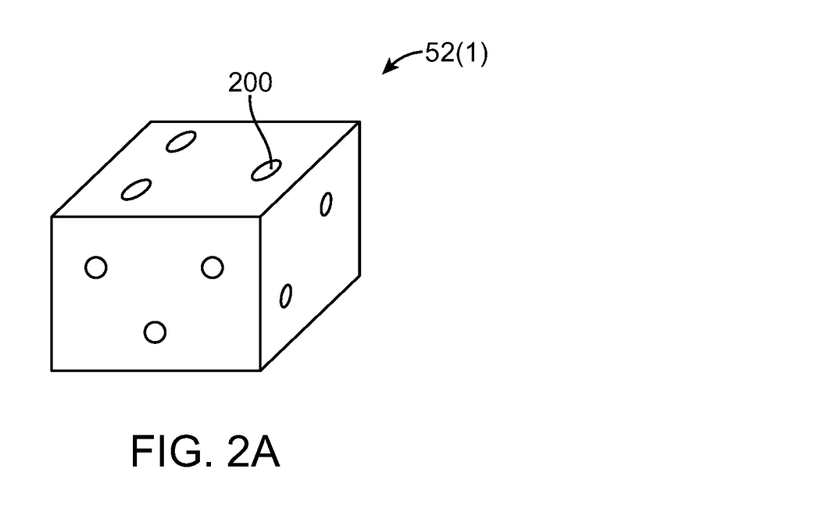
FIGS. 2A-2C shows marker blocks in accordance with various embodiments.
Figure 2B:
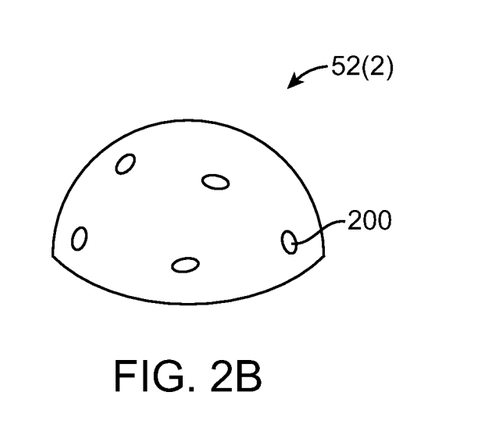
Figure 2C:
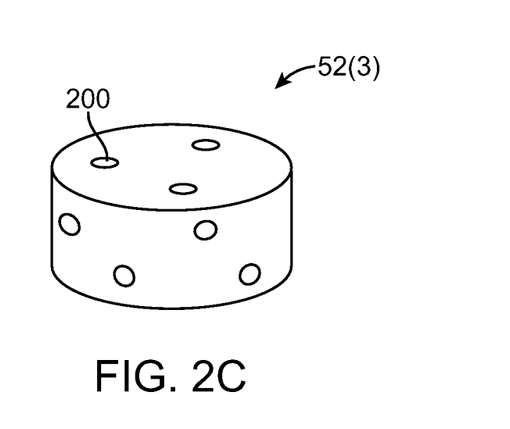

The optical device 50 may be a camera or other imaging devices, and is configured to generate an image of the marker block 52. The marker block 52 preferably comprises a reflective or retro-reflective material than can reflect light, whether in the visible or invisible wavelengths. FIG. 2A depicts an embodiment of a marker block 52(1) having a rectangular shape with multiple reference locations comprised of retro-reflective elements 200 located on its surface. FIG. 2B depicts an alternate marker block 52(2) having a hemispherical shape comprised of a plurality of retro-reflective elements 200 attached to its surface. FIG. 2C depicts another alternate marker block 52(3) having a disk shape. Marker block having other shapes may also be used so long as the size, spacing, and position of the reference locations are configured such that the optical device 50 can view and generate an image that accurately shows the positioning of the marker block 52.

When using the position monitoring system 18, one or more marker block 52 is placed on or secured to the patient 16, and the optical device 50 is used to sense the marker block 52. The optical device 50 produces a set of image coordinates for the marker elements 200 on the marker block 52. The position and distance of the marker elements 200 located on the marker block 52 is known relative to other marker elements 200 on the same marker block 52. By comparing the position and distance between the marker elements 200 on a recorded image frame with a reference position and image stored for the position monitoring system 18, the absolute position and orientation of the marker block 52 can be determined with a high degree of accuracy. This, in turn, provides an accurate position and orientation estimation for the patient position or the patient body position upon which the marker block 52 is attached. Such and similar physiological gating systems have been described in U.S. patent application Ser. No. 09/893,122, filed Jun. 26, 2001, the entire disclosure of which is expressly incorporated by reference herein.

Utilizing a video or optical based system for determining patient body position is advantageous in that it provides a reliable mechanism for repeating measurement results between uses on a given patient. In addition, such technique is noninvasive and no cables or connections must be made to the patient 16. Moreover, if use of the marker block 52 is impractical, the system can still be utilized without marker block 52 by performing measurements of physiological activity keyed to selected body landmarks which function as markers. Finally, such method is more accurate because it is based upon absolute measurement of external anatomical physical movement. The position monitoring system 18 is desirable for monitoring physiological movement due to breathing, the pattern and period of which are less predictable or consistent than those associated with cardiac movement. In other embodiments, instead of using optical-based sensing system, other types of respiratory sensor known in the art may be used. For example, in other embodiments, non-optical respiratory sensor(s), such as spirometer or a strain guage, may be used.

Figure 3:
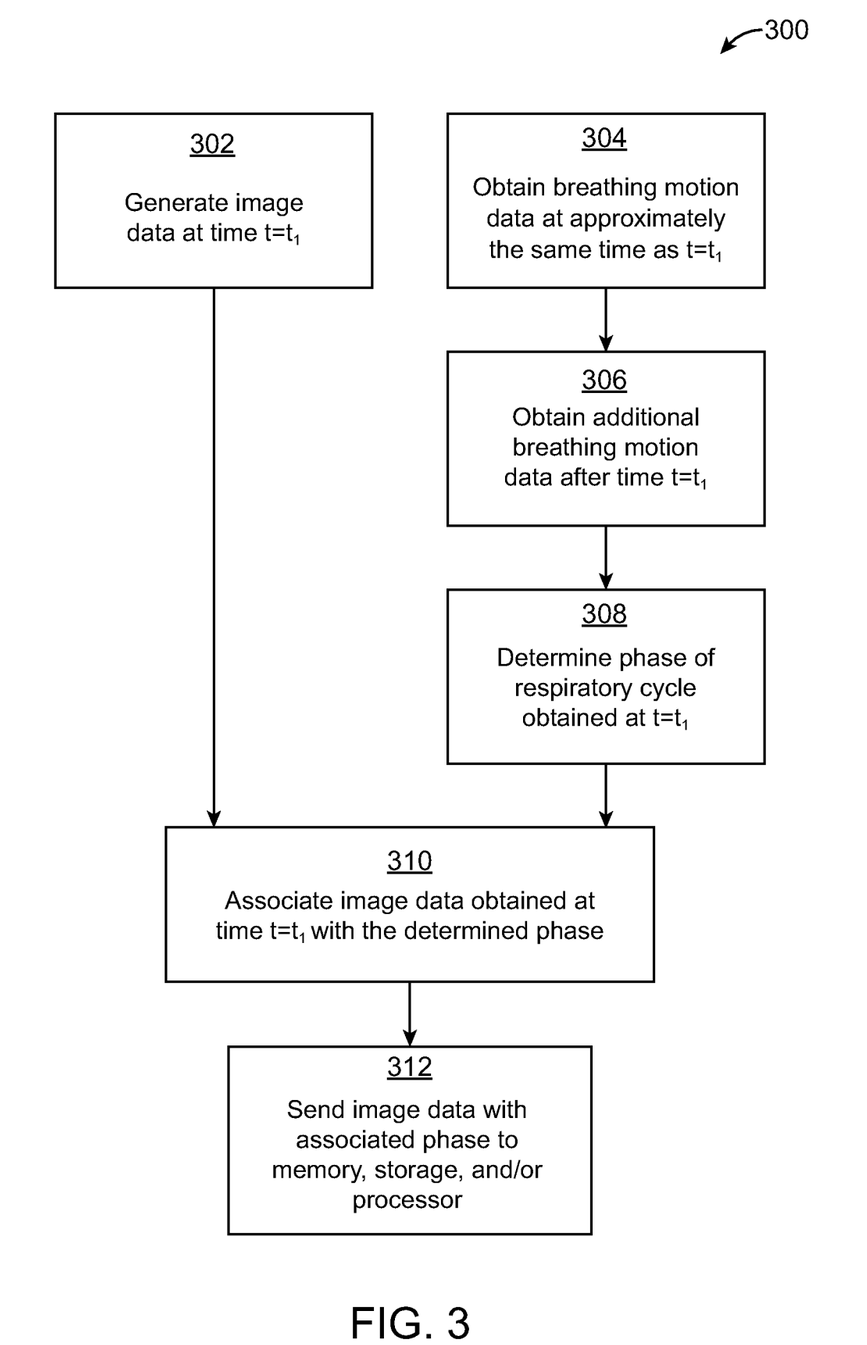
FIG. 3 illustrates a method of processing image data in accordance with some embodiments.

FIG. 3 illustrates a method 300 of processing image data in accordance with some embodiments. In some embodiments, the method 300 may be performed during an image acquisition session. As used in this specification, the term "image acquisition session" refers to a process for obtaining a set of image data. In some embodiments, the image acquisition session may be a process in which CT image data are obtained at two or more gantry angles. In other embodiments, the image acquisition session may be a process in which image data sufficient for use to reconstruct a three-dimensional image are obtained. For example, during such image acquisition session, image data are collected through a gantry range of 180°, and more preferably, through a gantry range of 360°. In further embodiments, the image acquisition session may be a process in which a video stream is created, wherein the video stream may be a sequence of two-dimensional images, or a sequence of three-dimensional images. Another example is the sequence of 2D projections acquired on a linac gantry for cone beam reconstruction.

Before the image acquisition session begins, the patient 16 is placed on the support 14, and the marker block 52 is coupled to the patient 16. In the illustrated embodiments, the marker block 52 is coupled to the chest of the patient 16. The image acquisition session then begins, in which the CT system 10 is used to generate image data for a portion of the patient 16 at time=$t_1$ (Step 302). In particular, the radiation source 20 is positioned at a gantry angle to deliver radiation towards the patient 16 to generate the image data.

While the CT system 10 is being operated to generate image data, breathing motion data is obtained using the position monitoring system 18 (Step 304). In the illustrated embodiments, the optical device 50 is used to obtain an image of the markers on the marker block 52. The image is then transmitted to a processor (e.g., processor 54) that processes the image to determine the position of the marker block 52. Systems and methods for determining a position of a marker block using an optical device is known in the art, and therefore, will not be described in detail.

After the image data is generated by the CT system 10 at t=$t_1$, the position monitoring system 18 continues to generate additional breathing motion data (Step 306). In the illustrated embodiments, the optical device 50 generate additional images of the marker block 52, and the additional images of the marker block 52 are analyzed by the processor 54 to track the positions of the marker block 52 as the patient 16 undergoes a respiratory cycle.

Figure 4A:
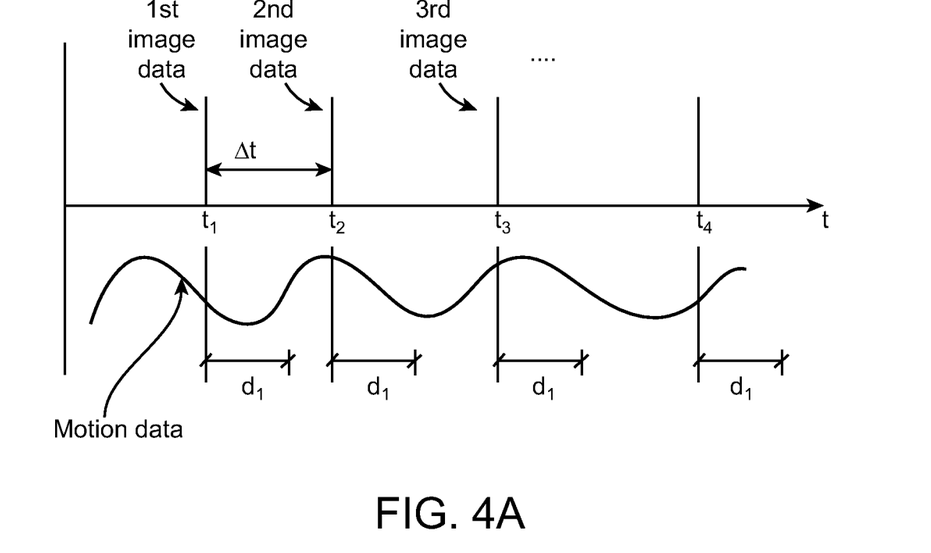
FIG. 4A illustrates a graph that shows a temporal relationship between a prescribed duration d1 and the time at which image data are obtained.

Next, the breathing motion data (or a subset of the breathing motion data) that are available as of time=$t_1$+d1 are used to determine a phase of a respiratory cycle that corresponds with the time t=$t_1$ at which the image data was obtained in Step 302 (Step 308). The amount of breathing motion data used may be prescribed in various ways. In some embodiments, after the image data at t=$t_1$ is generated by the system 10, the system 10 waits for the monitoring system 18 to generate motion data for a prescribed duration of time d1. When the prescribed duration d1 is reached, the system 10 then uses the breathing motion data that are available as of time=$t_1$+d1 to determine the phase of the respiratory cycle for the image data generated at t=$t_1$. FIG. 4A illustrates a graph that shows the temporal relationship between the prescribed duration d1 and the time at which image data are obtained. In other embodiments, instead of using a prescribed duration d1, after the image data at t=$t_1$ is generated by the system 10, the system 10 keeps track of the amount of breathing motion data generated by the position monitoring system 18 since then. When the amount of breathing motion data reaches a prescribed threshold (e.g., 50 kb), the breathing motion data that are available as of time=$t_1$+d1 are then used to determine the phase of the respiratory cycle for the image data generated at t=$t_1$.

In some embodiments, if the amount of breathing motion data for use to determine the phase is determined using prescribed duration d1, the prescribed duration d1 is set to be equal to at least a period P of breathing cycle, and more preferably, at least 1.5 times the period P of a breathing cycle. Such ensures that there are sufficient amplitude data to determine the phase value. In other embodiments, the prescribed duration d1 may be other factors times P. For example, d1 may be 2P or 3P in other embodiments. In some embodiments, for example, d1 may be a value that is between 5 seconds and 30 seconds, and more preferably, between 10 seconds and 15 seconds.

In further embodiments, the prescribed duration d1 may be tailored for each patient. In such cases, the actual breathing period of the patient may be measured for use to obtain d1 before image data is obtained. For example, a number (e.g., three) measurements of the breathing period may be obtained, and the period P for use to obtain may be the average of the values of the measurements. In some embodiments, measurement(s) that do not represent normal breathing pattern (e.g., due to patient's coughing) may be discarded and not use in the average calculation. For example, an operator or the processor 54 may determine that a breathing pattern is normal, and store the breathing pattern as a reference pattern. Subsequent patient's breathing patterns are then compared (e.g., pattern matched) against the reference pattern to determine whether the subsequent breathing patterns are normal. If a subsequent breathing pattern deviates from the reference breathing pattern (e.g., deviates from periodicity), then the subsequent breathing pattern may be considered as not normal. Systems and methods for detecting deviation from periodicity has been described in U.S. patent application Ser. No. 10/678, 741, entitled, "Method and system for radiation application."

Figure 5:
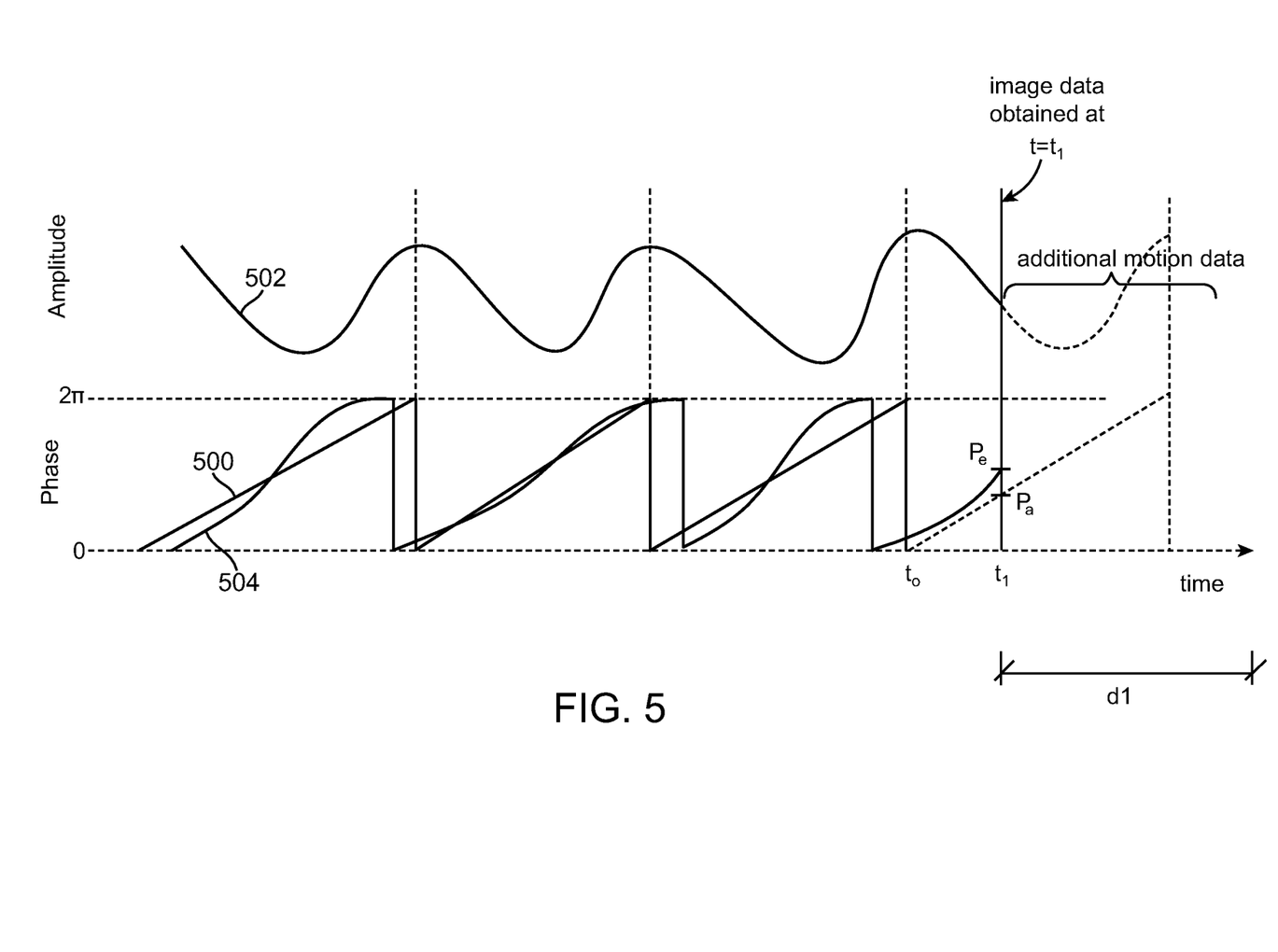
FIG. 5 illustrates an example of breathing motion data and corresponding phase graph superimposed thereon.

Various techniques may be used to determine the phase of respiratory cycle for the image data obtained at t=$t_1$. In the illustrated embodiments, the breathing motion data comprises breathing amplitude values. In step 308, by determining a plurality of amplitude positions of the marker block 52 over a period of time, the processor 54 can be configured to obtain a plurality of phase points that correspond to different levels of completeness of a breathing cycle at various time points. For example, a phase value may have a value from 0° to 360° ($2\pi$), with 0° and 360° corresponding to the vicinity of inhale extreme of the respiration signal. FIG. 5 shows an example of a phase value chart 500 for breathing signal samples superimposed on an example of respiration amplitude signal 502. As shown in the figure, by determining the inhale extreme of the respiration signal, the points that correspond to phase values of 0° and 360° can be obtained. The remaining phase values between 0° and 360° are then determined as linear interpolation between the two points that correspond to the phase values, 0° and 360°. In other embodiments, instead of the vicinity of inhale extreme, the phase values 0° and 360° can correspond to other point of the respiration signal.

As shown in FIG. 5, at time t=$t_1$, the image data is obtained. The motion data that are available as of time t=$t_1$, is insufficient to determine accurately the phase value that corresponds to the image data at $t=t_1$. This is because the respiratory cycle that started at $t=t_0$ is not completed yet as of time $t=t_1$. The phase may be estimated using the motion data that are available as of time $t=t_1$. FIG. 5 also shows an estimated phase curve that represents a real time estimate of a phase value at various time points. As shown in the figure, at time $t=t_1$, the estimated phase value is Pe. However, using the above technique, additional motion data is obtained within d1, and the motion data that are available as of time $t=t_1+d1$ can then be used to determine the actual (or more precise) phase value for the image data that is collected at $t=t_1$. As shown in the example, the actual phase value is Pa.

Returning to FIG. 3, next, the determined phase is associated with the image data obtained in Step 302 (Step 310). The image data and the associated phase are then sent downstream for storage or processing (Step 312). For example, the image data and the associated phase may be sent to a computer-readable medium for storage (such as that associated with processor 54) so that they can be processed and/or examined at a later time. For example, the determined phase value may be used in a procedure to determine a treatment plan for the patient 16.

In the illustrated embodiments, the method of 300 is repeated for time $t=t_2, t_3$, etc., to collect additional CT image data until all CT image data are obtained. For example, the gantry 12 of the CT system 10 can make additional revolution(s) about the patient 16 to collect additional image data until all required image data associated with all phases (or prescribed phase(s)) of a physiological cycle have been obtained.

Figure 4B:
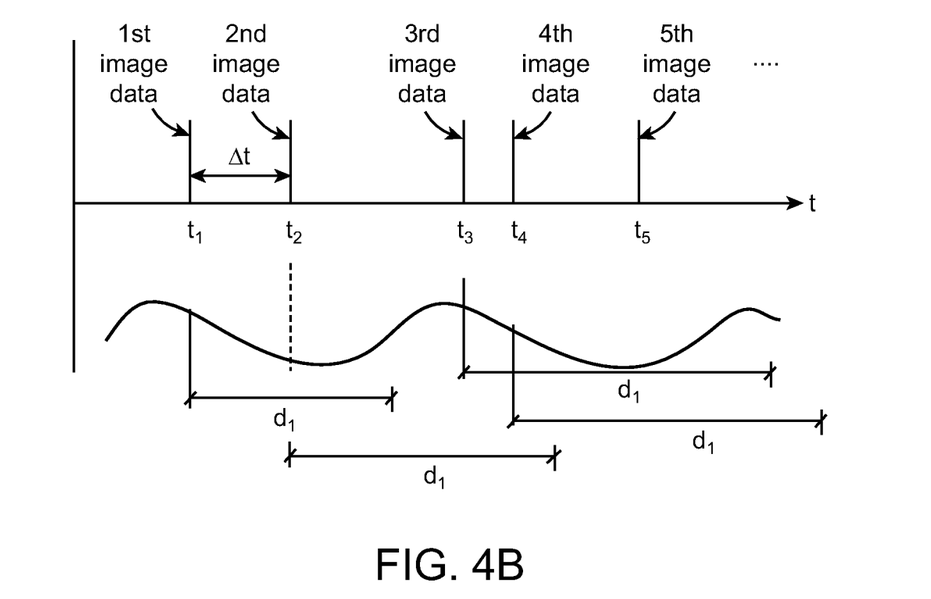
FIG. 4B illustrates a graph that shows a temporal relationship between a prescribed durations d1, d2 and the time at which image data are obtained.

As shown in FIG. 4A, the prescribed duration d1 is less than Δt, which corresponds to a difference in period between two image acquisition time. However, in other embodiments, the prescribed duration d1 may be longer than Δt (FIG. 4B). Also, in any of the embodiments described herein, the duration Δt between two CT image acquisition times needs not be constant. For example, $\Delta t_1$ that is the duration between first and second CT image data acquisition times ($\Delta t_1=t_2-t_1$) may be different from the duration $\Delta t_2$ between second and third CT image data acquisition times ($\Delta t_2=t_3-t_2$).

In some embodiments, the image data can be sorted or processed such that image data associated with a phase range of a physiological cycle are grouped together, or associated with each other. A processor and/or a software can be configured to perform such function and to select CT image data that are associated with a same phase range of a physiological cycle. In the illustrated embodiments, the processor 54 (or another processor) is configured to use the determined phase value to bin CT image data obtained by the system 10. For example, in some embodiments, a respiratory cycle may be divided into N=4 phase intervals or time bins, with N=1 corresponding to phase values between 0° and 90° (including 90°), N=2 corresponding to phase values between 90° and 180° (including 180°), N=3 corresponding to phase values between 180° and 270° (including 270°), and N=4 corresponding to phase values between 270° and 360° (including 360°). In such case, the determined phase value in step 308 may be used (e.g., by the processor 54) to bin the CT image data obtained in step 302 to the appropriate time bin. For example, if the determined phase value in step 308 is 182°, then the CT image data determined in step 302 will be binned to the phase interval or time bin that corresponds to N=3. In other embodiments, N can be values other than "4." In some embodiments, the binning of the image data is considered to be a part of the image acquisition process. In other embodiments, the binning of the image data is not a part of the image acquisition process if it is performed at a much later time (e.g., days after).

In some embodiments, the image data associated with different phases of a physiological movement of the patient 16 are used to construct volumetric images for the respective phases. In such cases, image data that are associated with a same phase or phase range of a physiological cycle (e.g., image data that are binned in the same bin) are selected to construct a volumetric image for that phase or phase range. In some cases, the constructed volumetric images for the various phases or phase ranges may be displayed consecutively to form a video stream.

In some embodiments, the act of determining the phase (Step 308), the act of associating the determined phase with the CT image data (Step 310), and/or the act of sending the associated phase and CT image data for storage or processing (Step 312), is performed before the image acquisition session is completed. In some cases, the image acquisition session is considered completed when the patient 16 leaves the patient support. In other cases, the image acquisition session is considered completed when the position monitoring system 18 stops collecting positional data. In other embodiments, the image acquisition session is considered completed when all desired CT image data are collected by the system 10.

In some embodiments, the act of determining the phase (Step 308), the act of associating the determined phase with the CT image data (Step 310), and/or the act of sending the associated phase and CT image data for storage or processing (Step 312), may be performed within 60 seconds, and preferably within 15 seconds, and more preferably within 5 seconds, after the CT image data is obtained in step 302. Also, in some embodiments, the act of determining the phase (Step 308), the act of associating the determined phase with the CT image data (Step 310), and/or the act of sending the associated phase and CT image data for storage or processing (Step 312), may be performed after the radiation source 20 rotates 180°, but before the radiation source 20 completes another 180° rotation. In other embodiments, the act of determining the phase (Step 308), the act of associating the determined phase with the CT image data (Step 310), and/or the act of sending the associated phase and CT image data for storage or processing (Step 312), may be performed after the radiation source 20 rotates 360°, but before the radiation source 20 completes another 360° rotation. In further embodiments, the act of determining the phase (Step 308), the act of associating the determined phase with the CT image data (Step 310), and/or the act of sending the associated phase and CT image data for storage or processing (Step 312), may be performed after sufficient CT image data have been obtained to reconstruct a three-dimensional image for one phase of the respiratory cycle, but before sufficient CT image data are obtained to reconstruct another three-dimensional image for another phase of the respiratory cycle.

In other embodiments, the act of determining the phase (Step 308) may be performed before the image acquisition process is completed, but the act of associating the determined phase with the CT image data (Step 310) and the act of sending the associated phase and CT image data for storage or processing (Step 312) are performed after the image acquisition process is completed.

In further embodiments, the act of determining the phase (Step 308) and the act of associating the determined phase with the CT image data (Step 310) may be performed before the image acquisition process is completed, but the act of sending the associated phase and CT image data for storage or processing (Step 312) is performed after the image acquisition process is completed.

In the above technique, the phase that corresponds to CT image data generated at a certain time (e.g., $t=t_1$) is retrospectively calculated using actual motion data generated that are available, e.g., as of time $t=t_1+d1$. Such technique provides an accurate determination of phase values, because it uses actual motion data to retrospectively calculate the phases at various time points. Also, such technique is advantageous in that the image data that has been associated with a phase value is available to a user before the image acquisition process is completed.

Although the above embodiments have been described with reference to CT (which may, for example, include CBCT), it should be noted that the scope of the invention should not be so limited. In alternative embodiments, similar methods can be carried out using a MRI machine, a PET machine, or a SPECT machine.

For example, in other embodiments, the system 10 may include a PET machine, and the above technique may be used to bin PET image data collected at certain time (e.g., $t=t_1$) to a correct phase bin. In such cases, after the PET image data is obtained at certain time (e.g., $t=t_1$), the system 10 waits for a prescribed duration (e.g., d1) to collect additional motion data. The system 10 then uses the motion data that are available as of $t=t_1+d1$ to determine the phase that corresponds with the PET image data. The determined phase is then used to bin the PET image data in the correct phase bin. For example, if the respiratory phase is divided into 4 bins (e.g., bin 1=0°-90°, bin 2=90°-180°, bin 3=180°-270°, and bin 4=270°-360°), and the determined phase for a PET image data is calculated to be 96°, then the PET image data will be binned to the second phase bin, i.e., bin 2. The above process repeats for the next PET image data (whose acquisition time, e.g., $t=t_2$, depends on the occurrence of the next event), until the image acquisition process is completed. Such technique is advantageous in that the binned PET image data is available to a user before the image acquisition process is completed. Also, the above described technique provides an accurate determination of phase values, because it uses actual motion data to retrospectively calculate the phases at various time points.

In addition, instead of obtaining breathing motion data of a patient, other types of motion data may be obtained. For example, in other embodiments, the motion data are those resulted from heart beat.

Computer System Architecture

Figure 6:
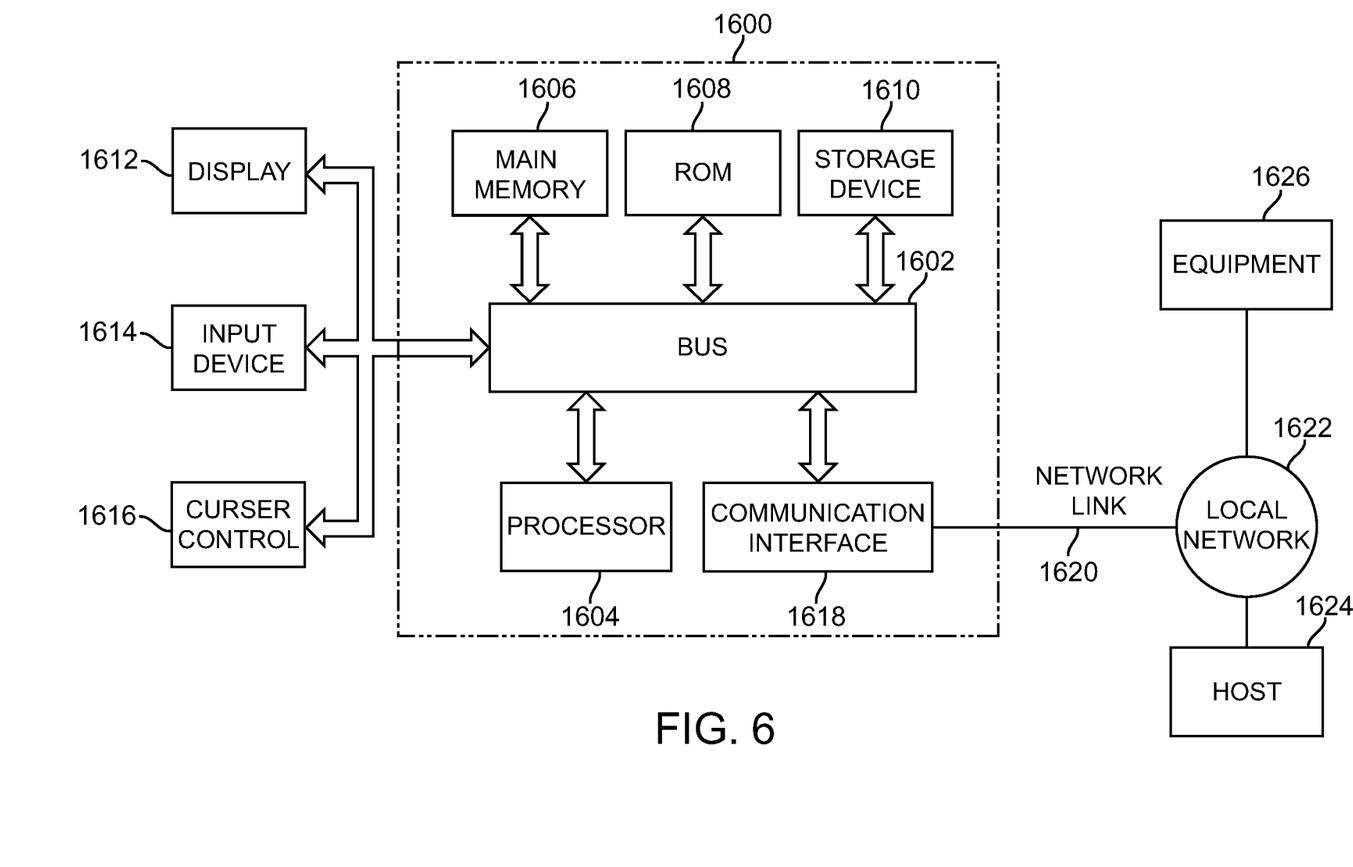
FIG. 6 is a diagram of a computer hardware system with which embodiments described herein may be implemented.

FIG. 6 is a block diagram illustrating an embodiment of a computer system 1600 that can be used to implement various embodiments described herein. Computer system 1600 includes a bus 1602 or other communication mechanism for communicating information, and a processor 1604 coupled with the bus 1602 for processing information. The processor 1604 may be an example of the processor 54 of FIG. 1, or an example of any processor described herein. The computer system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The computer system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The computer system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the computer system 1600 can be used to perform various functions described herein. According to some embodiments, such use is provided by computer system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another computer-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "computer-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. Volatile media includes dynamic memory, such as the main memory 1606. Transmission media includes coaxial cables, copper wire and fiber optics, including the wires that comprise the bus 1602. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the computer system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The computer system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the computer system 1600, are exemplary forms of carrier waves transporting the information. The computer system 1600 can send messages and receive data, including program code, through the network (s), the network link 1620, and the communication interface 1618.

Although particular embodiments have been shown and described, it will be understood that they are not intended to limit the present inventions, and it will be obvious to those skilled in the art that various changes and modifications may be made without departing from the spirit and scope of the present inventions. For example, the term "image" as used in this specification includes image data that may be stored in a circuitry or a computer-readable medium, and should not be limited to image data that is displayed visually. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A method of processing image data, comprising:
   obtaining image data, wherein the image data is obtained at time t;
   determining a phase of a respiratory cycle using a hardware processor, wherein the phase is determined at a time that is after the time t, and corresponds to a first level of completeness of the respiratory cycle;
   associating the image data with the determined phase within 60 seconds after the image data is obtained;
   obtaining additional image data;
   determining an additional phase of the respiratory cycle corresponding to a second level of completeness of the respiratory cycle that is different from the first level; and
   associating the additional image data with the additional phase;
   wherein the phase and the additional phase with which the image data and the additional image data are respectively associated are different; and
   wherein the image data and the additional image data are generated at respective times corresponding to the different phases of the respiratory cycle.

2. The method of claim 1, wherein the phase is determined by obtaining one or more amplitudes of the breathing cycle; and using the one or more amplitudes to determine the phase.

3. The method of claim 1, wherein the image data is associated with the determined phase within 15 seconds after the image data is obtained.

4. The method of claim 1, wherein the image data is associated with the determined phase within 5 seconds after the image data is obtained.

5. The method of claim 1, wherein the image data is obtained by performing a computed tomography procedure, an MRI procedure, a PET procedure, or a SPECT procedure.

6. The method of claim 1, wherein the phase is determined by: obtaining breathing motion data; and comparing the breathing motion data with a reference set of data.

7. The method of claim 1, wherein the image data is associated with the determined phase before an image acquisition session to obtain a set of images is completed.

8. The method of claim 1, wherein the determined phase corresponds to the time t.

9. The method of claim 8, wherein the phase corresponding to the time t is determined using at least some data regarding respiratory motion that occurs after the time t.

10. The method of claim 1, further comprising using the image data to reconstruct a three dimensional image.

11. The method of claim 10, further comprising displaying at least a portion of the three dimensional image as a part of a video stream.

12. A system for processing image data, comprising a processor that is configured for:
    obtaining image data that is generated at time t;
    determining a phase of a respiratory cycle at a time that is after the time t, and corresponds to a first level of completeness of the respiratory cycle;
    associating the image data with the determined phase within 60 seconds after the image data is obtained;
    obtaining additional image data;
    determining an additional phase of the respiratory cycle corresponding to a second level of completeness of the respiratory cycle that is different from the first level; and
    associating the additional image data with the additional phase;
    wherein the phase and the additional phase with which the image data and the additional image data are respectively associated are different; and
    wherein the image data and the additional image data are generated at respective times corresponding to the different phases of the respiratory cycle.

13. The system of claim 12, wherein the processor is configured to determine the phase by obtaining one or more amplitudes of the breathing cycle; and using the one or more amplitudes to determine the phase.

14. The system of claim 12, wherein the processor is configured to associate the image data with the determined phase within 15 seconds after the image data is obtained.

15. The system of claim 12, wherein the processor is configured to associate the image data with the determined phase within 5 seconds after the image data is obtained.

16. The system of claim 12, wherein the phase represents a degree of completeness of the respiratory cycle.

17. The system of claim 12, wherein the image data is associated with the determined phase before an image acquisition session to obtain a set of images is completed.

18. The system of claim 12, wherein the determined phase corresponds to the time t.

19. The system of claim 18, wherein the processor is configured to determine the phase corresponding to the time t using at least some data regarding respiratory motion that occurs after the time t.

20. The system of claim 12, wherein the image data is generated by performing a computed tomography procedure, an MRI procedure, a PET procedure, or a SPECT procedure.

21. The system of claim 20, wherein the processor is configured to determine the phase by: obtaining breathing motion data; and comparing the breathing motion data with a reference set of data.

22. The system of claim 12, wherein the processor is further configured to use the image data to reconstruct a three dimensional image.

23. The system of claim 22, wherein the processor is further configured to cause at least a portion of the three dimensional image to be displayed as a part of a video stream.

24. A method of processing image data, comprising:
obtaining image data during an image acquisition session;
determining a phase of a respiratory cycle using a hardware processor, wherein the phase corresponds to a first level of completeness of the respiratory cycle;
associating the image data with the determined phase after the image data is obtained but before the image acquisition session is completed;
obtaining additional image data;
determining an additional phase of the respiratory cycle corresponding to a second level of completeness of the respiratory cycle that is different from the first level; and
associating the additional image data with the additional phase;
wherein the phase and the additional phase with which the image data and the additional image data are respectively associated are different; and
wherein the image data and the additional image data are generated at respective times corresponding to the different phases of the respiratory cycle.

25. The method of claim 24, wherein the phase is determined by obtaining one or more amplitudes of the breathing cycle; and using the one or more amplitudes to determine the phase.

26. The method of claim 24, wherein the image data is associated with the determined phase within 15 seconds after the image data is obtained.

27. The method of claim 24, wherein the image data is associated with the determined phase within 5 seconds after the image data is obtained.

28. The method of claim 24, wherein the image data is obtained by performing a computed tomography procedure, an MRI procedure, a PET procedure, or a SPECT procedure.

29. The method of claim 24, wherein the phase is determined by: obtaining breathing motion data; and comparing the breathing motion data with a reference set of data.

30. The method of claim 24, wherein the image acquisition session comprises a process to obtain a set of image data, the set of image data comprising the image data and the additional image data.

31. The method of claim 24, wherein the image acquisition session comprises a process to collect an amount of data that is sufficient for reconstructing a volumetric image.

32. The method of claim 24, wherein the image acquisition session comprises a process to collect an amount of data that is sufficient to form a video stream.

33. The method of claim 24, wherein the image data is obtained at time t, the determined phase corresponds to the time t, and the phase is determined at a time that is after t.

34. The method of claim 33, wherein the phase corresponding to the time t is determined using at least some data regarding respiratory motion that occurs after the time t.

35. The method of claim 24, further comprising using the image data to reconstruct a three dimensional image.

36. The method of claim 35, further comprising displaying at least a portion of the three dimensional image as a part of a video stream.

37. A system for processing image data, comprising a processor that is configured for:
obtaining image data during an image acquisition session;
determining a phase of a respiratory cycle, wherein the phase corresponds to a first level of completeness of the respiratory cycle;
associating the image data with the determined phase after the image data is obtained but before the image acquisition session is completed;
obtaining additional image data;
determining an additional phase of the respiratory cycle corresponding to a second level of completeness of the respiratory cycle that is different from the first level; and
associating the additional image data with the additional phase;
wherein the phase and the additional phase with which the image data and the additional image data are respectively associated are different; and
wherein the image data and the additional image data are generated at respective times corresponding to the different phases of the respiratory cycle.

38. The system of claim 37, wherein the processor is configured to determine the phase by obtaining one or more amplitudes of the breathing cycle; and using the one or more amplitudes to determine the phase.

39. The system of claim 37, wherein the processor is configured to associate the image data with the determined phase within 15 seconds after the image data is obtained.

40. The system of claim 37, wherein the processor is configured to associate the image data with the determined phase within 5 seconds after the image data is obtained.

41. The system of claim 37, wherein the image data is generated by performing a computed tomography procedure, an MRI procedure, a PET procedure, or a SPECT procedure.

42. The system of claim 37, wherein the image acquisition session comprises a process to obtain a set of image data, the set of image data comprising the image data and the additional image data.

43. The system of claim 37, wherein the image acquisition session comprises a process to collect an amount of data that is sufficient for reconstructing a volumetric image.

44. The system of claim 37, wherein the image acquisition session comprises a process to collect an amount of data that is sufficient to form a video stream.

45. The system of claim 37, wherein the image data is generated at time t, the determined phase corresponds to the time t, and the processor is configured to determine the phase at a time that is after t.

46. The system of claim 45, wherein the processor is configured to determine the phase corresponding to the time t using at least some data regarding respiratory motion that occurs after the time t.

47. The system of claim 37, wherein the phase represents a degree of completeness of the respiratory cycle.

48. The system of claim 47, wherein the processor is configured to determine the phase by: obtaining breathing motion data; and comparing the breathing motion data with a reference set of data.

49. The system of claim 37, wherein the processor is further configured to use the image data to reconstruct a three dimensional image.

50. The system of claim 49, wherein the processor is further configured to cause at least a portion of the three dimensional image to be displayed as a part of a video stream.

* * * * *